United States Patent [19]

Petitpierre

[11] 4,287,336

[45] Sep. 1, 1981

[54] CHROMOGENIC PROPENYLENESULFONE COMPOUNDS

[75] Inventor: Jean C. Petitpierre, Kaiseraugst, Switzerland

[73] Assignee: Ciba-Geigy Corporation, Ardsley, N.Y.

[21] Appl. No.: 73,758

[22] Filed: Sep. 10, 1979

[30] Foreign Application Priority Data

Sep. 22, 1978 [CH] Switzerland .................. 9954/78

[51] Int. Cl.³ .................. C07C 401/10; C07C 403/10; C07C 403/06
[52] U.S. Cl. .................. 542/472; 260/465 E; 542/427; 542/469; 564/306; 564/384; 564/391; 564/431; 564/433; 564/434
[58] Field of Search .................. 542/469, 472, 427; 260/570.9, 576, 573, 571, 578, 465 E; 564/306, 384, 391, 431, 433, 434

[56] References Cited

U.S. PATENT DOCUMENTS

3,265,497  8/1966  Kosche ................................. 260/576
3,879,463  4/1975  Peters et al. ......................... 260/576

OTHER PUBLICATIONS

Schmidt et al., Annalen 623, (1954), pp. 204–216.

*Primary Examiner*—Arthur P. Demers
*Attorney, Agent, or Firm*—Edward McC. Roberts; John P. Spitals

[57] ABSTRACT

Chromogenic compounds of the formula

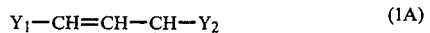
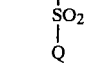

or

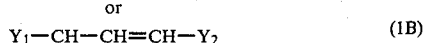
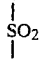

wherein each of $Y_1$ and $Y_2$ independently represents an amino-substituted phenyl radical of the formula

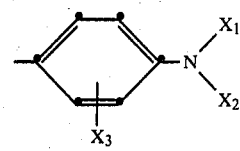

a 3-indolyl radical of the formula

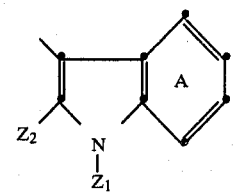

or a 3-carbazolyl radical of the formula

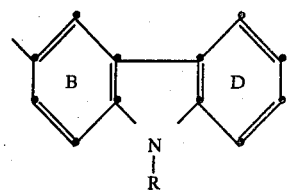

and Q represents alkyl of 1 to 12 carbon atoms or unsubstituted or substituted aryl or aralkyl, while each of $X_1$ and $X_2$ independently represents hydrogen, alkyl containing not more than 12 carbon atoms which is unsubstituted or substituted by halogen, hydroxyl, cyano or lower alkoxy, or represents cycloalkyl, phenyl, benzyl, or phenyl or benzyl which is substituted by halogen, lower alkyl or lower alkoxy, or $X_1$ and $X_2$ together with the nitrogen atom to which they are attached represent a 5- or 6-membered heterocyclic radical, $X_3$ represents hydrogen, halogen, nitro, lower alkyl or lower alkoxy, each of R and $Z_1$ independently represents hydrogen, alkyl containing not more than 12 carbon atoms which is unsubstituted or substituted by halogen, hydroxyl, cyano or lower alkoxy, or represents alkenyl containing not more than 12 carbon atoms, acyl of 1 to 12 carbon atoms, phenyl, benzyl, or phenyl or benzyl which is substituted by halogen, lower alkyl, lower alkoxy or nitro, and $Z_2$ represents hydrogen, lower alkyl or phenyl, and the rings A, B and D, each independently of the other, can be unsubstituted or substituted by cyano, nitro, halogen, lower alkyl, lower alkoxy or lower alkoxycarbonyl, and the ring D can also contain an unsubstituted or substituted phenyl radical or a fused benzene ring.

These compounds are particularly suitable for use as color formers in pressure-sensitive or heat-sensitive recording materials.

16 Claims, No Drawings

CHROMOGENIC PROPENYLENESULFONE COMPOUNDS

The present invention relates to chromogenic propenylenesulfone compounds, a process for their manufacture and their use as colour formers in pressure-sensitive or heat-sensitive recording material.

The novel chromogenic sulfone compounds have the general formula

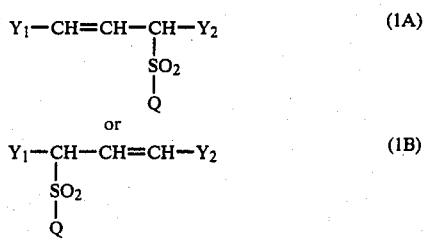

wherein each of $Y_1$ and $Y_2$ independently represents an amino-substituted phenyl radical of the formula

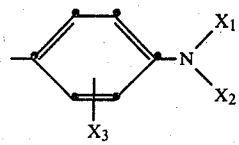

a 3-indolyl radical of the formula

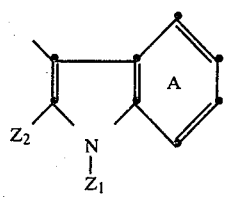

a 3-carbazolyl radical of the formula

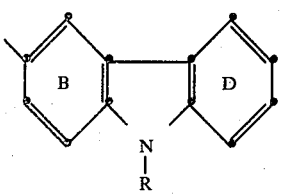

and Q represents alkyl of 1 to 12 carbon atoms or unsubstituted or substituted aryl or aralkyl, whilst each of $X_1$ and $X_2$ independently represents hydrogen, alkyl containing not more than 12 carbon atoms which is unsubstituted or substituted by halogen, hydroxyl, cyano or lower alkoxy, or represents cycloalkyl, phenyl, benzyl, or phenyl or benzyl which is substituted by halogen, lower alkyl or lower alkoxy, or $X_1$ and $X_2$ together with the nitrogen atom to which they are attached represent a 5- or 6-membered heterocyclic radical, $X_3$ represents hydrogen, halogen, nitro, lower alkyl or lower alkoxy, each of R and $Z_1$ independently represents hydrogen, alkyl containing not more than 12 carbon atoms which is unsubstituted or substituted by halogen, hydroxyl, cyano or lower alkoxy, or represents alkenyl containing not more than 12 carbon atoms, acyl of 1 to 12 carbon atoms, phenyl, benzyl, or phenyl or benzyl which is substituted by halogen, lower alkyl, lower alkoxy or nitro, and $Z_2$ represents hydrogen, lower alkyl or phenyl, and the rings A, B and D, each independently of the other, can be unsubstituted or substituted by cyano, nitro, halogen, lower alkyl, lower alkoxy or lower alkoxycarbonyl, and the ring D can also contain an unsubstituted or substituted phenyl radical or a fused benzene ring.

Preferred propenylenesulfone compounds of the formula (1) are those in which $Y_1$ and $Y_2$ are amino-substituted phenyl radicals of the formula (1a) or 3-carbazolyl radicals of the formula (1c).

In the definition of the radicals of the sulfone compounds, lower alkyl and lower alkoxy usually denote those groups or group components which contain 1 to 5, in particular 1 to 3, carbon atoms. Lower alkyl is e.g. methyl, ethyl, n-propyl, isopropyl, n-butyl, sec-butyl, tert-butyl, or amyl, and lower alkoxy is e.g. methoxy, ethoxy or isopropoxy.

The term "aryl" denotes preferably phenyl. Acyl is in particular formyl, lower alkylcarbonyl, for example acetyl or propionyl, or benzoyl. Further acyl radicals are lower alkylsulfonyl, for example methylsulfonyl or ethylsulfonyl, and phenylsulfonyl. Phenyl, benzoyl and phenylsulfonyl can be substituted e.g. by halogen, methyl, methoxy or ethoxy.

The radicals $Y_1$ and $Y_2$ can be different. For example, $Y_1$ is a radical of the formula (1a) and $Y_2$ is a radical of the formula (1a) which is different from $Y_1$ or is a 3-indolyl radical of the formula (1b) or a 3-carbazolyl radical of the formula (1c). Preferably, however, $Y_1$ and $Y_2$ are identical radicals. Q is preferably an unsubstituted or substituted aryl radical.

Alkyl radicals represented by R, $X_1$, $X_2$ and $Z_1$ can be straight chain or branched. Examples of such alkyl radicals are: methyl, ethyl, n-propyl, isopropyl, n-butyl, sec-butyl, n-hexyl, n-octyl or n-dodecyl.

Substituted alkyl radicals represented by R, $X_1$, $X_2$ and $Z_1$ are in particular cyanoalkyl, haloalkyl, hydroxyalkyl, alkoxyalkyl, each containing a total of 2 to 4 carbon atoms, for example β-cyanoethyl, β-chloroethyl, β-hydroxyethyl, β-methoxyethyl or β-ethoxyethyl.

Cycloalkyl represented by $X_1$ and $X_2$ is for example cyclopentyl or preferably cyclohexyl.

Preferred substituents in the benzyl and phenyl moiety of the X, $Z_1$ and R radicals are e.g. halogen atoms, or methyl or methoxy groups. Examples of such araliphatic and aromatic radicals are: p-methylbenzyl, o- or p-chlorobenzyl, o- or p-tolyl, xylyl, o-, m- or p-chlorophenyl or o- or p-methoxyphenyl.

A heterocyclic radical represented by $X_1$ and $X_2$ together with the nitrogen atom to which they are attached is e.g. pyrrolidino, piperidino, pipecolino, morpholino, thiomorpholino or piperazino.

Alkenyl represented by R and $Z_1$ is e.g. allyl, 2-methallyl, 2-ethallyl, 2-butenyl or octenyl.

An acyl radical within the definition of R and $Z_1$ is in particular formyl, lower alkylcarbonyl, for example acetyl or propionyl, or also benzoyl. Benzoyl can be substituted in the benzene ring by halogen, methyl or methoxy.

Each of $X_1$, $X_2$ and Z independently represents preferably lower alkyl or benzyl, whilst $Z_2$ preferably represents methyl or phenyl. Advantageously, $X_1$ and $X_2$ can also represent phenyl, lower alkylphenyl or lower alkoxyphenyl. $X_3$ preferably represents hydrogen, methyl, methoxy or chlorine. R is preferably alkyl of 1 to 8 carbon atoms or benzyl and, in particular, ethyl, n-butyl or n-octyl.

As alkyl, Q can have the same meanings as those assigned to the X, Z and R radicals. As aralkyl, Q is preferably benzyl or phenylethyl.

An aryl radical represented by Q can be phenyl, diphenyl or naphthyl. These aromatic carbocyclic groups, and especially phenyl, can contain halogen, cyano, nitro, lower alkyl, lower alkoxy, methylenedioxy or acyl of 1 to 8 carbon atoms. Particularly preferred acyl radicals are alkanoyl radicals of 2 to 4 carbon atoms, such as acetyl or propionyl.

As an aryl radical, Q is preferably phenyl or phenyl which is substituted by halogen, methoxy or methyl. Examples of these aryl radicals are: phenyl, o-, m- or p-methylphenyl, o-, m- or p-methoxyphenyl, o-, m- or p-chlorophenyl, o-, m- or p-bromophenyl or o-, m- or p-fluorophenyl, 3,4-dimethoxyphenyl, 3,4-dichlorophenyl, and naphthyl.

The rings A, B and D are preferably not further substituted. If they do contain substituents, each independently of the other is further substituted in particular by halogen, lower alkyl or lower alkoxy, e.g. by chlorine, methyl or methoxy. Advantageously, each benzene ring can contain 1 or 2 substituents. The substituents of the rings A and D are preferably in the para-position to the nitrogen atom. The ring D can also contain one or two fused benzene nuclei, which thus complete e.g. a 1,2-benzocarbazole, 3,4-benzocarbazole or 1,2,3,4-dibenzocarbazole ring.

Chromogenic propenylenesulfone compounds having an interesting utility are those of the formula $$Y_3\text{—CH}=\text{CH—CH—}Y_4 \text{ (2A) or } Y_3\text{—CH—CH}=\text{CH—}Y_4 \text{ (2B)}$$
$$\begin{array}{c} | \\ SO_2 \\ | \\ Q_1 \end{array} \qquad \begin{array}{c} | \\ SO_2 \\ | \\ Q_1 \end{array}$$

wherein each of $Y_3$ and $Y_4$ independently represents an amino-substituted phenyl radical of the formula

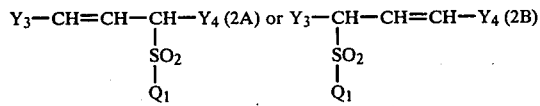

(2a)

a 3-indolyl radical of the formula

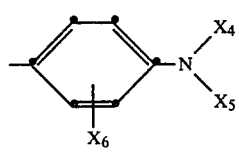

(2b)

or a 3-carbazolyl radical of the formula

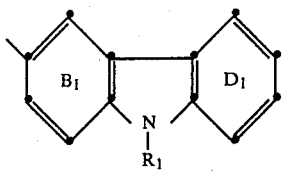

(2c)

and $Q_1$ represents alkyl of 1 to 12 carbon atoms, preferably lower alkyl, or an unsubstituted or substituted aryl radical, whilst each of $X_4$ and $X_5$ independently represents lower alkyl, phenyl, lower alkylphenyl, lower alkoxyphenyl or benzyl, and $X_4$ also represents hydrogen, or $X_4$ and $X_5$ together with the nitrogen atom to which they are attached represent pyrrolidino, piperidino or morpholino, $X_6$ represents hydrogen, halogen, lower alkyl or lower alkoxy, each of $R_1$ and $Z_3$ independently represents alkyl of not more than 12 carbon atoms which is unsubstituted or substituted by halogen, cyano or lower alkoxy, or represents lower alkylcarbonyl, phenyl, or benzyl which is unsubstituted or substituted by halogen, lower alkyl or lower alkoxy, and $Z_3$ also represents hydrogen and $Z_4$ represents hydrogen, methyl or phenyl, and the rings $A_1$, $B_1$ and $D_1$, each independently of the other, can be unsubstituted or substituted by cyano, halogen, lower alkyl or lower alkoxy and the ring $D_1$ can also contain one or two fused benzene nuclei.

Preferred sulfone compounds of the formula (2) are those in which $Y_3$ and $Y_4$ are amino-substituted phenyl radicals of the formula (2a) or 3-carbazolyl radicals of the formula (2c). $Q_1$ preferably represents phenyl or phenyl which is substituted by halogen, methyl or methoxy.

Particularly interesting sulfone compounds are those of the formulae

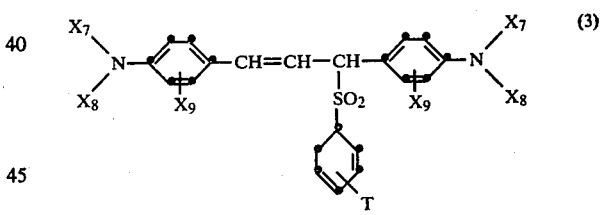

wherein $X_7$ represents lower alkyl, phenyl, lower alkylphenyl, lower alkoxyphenyl or benzyl, $X_8$ represents hydrogen, lower alkyl or benzyl, $X_9$ represents hydrogen, methyl, methoxy or ethoxy, T represents hydrogen, halogen, methyl or methoxy, $Z_4$ represents hydrogen, methyl or phenyl, $Z_5$ represents hydrogen, acetyl, alkyl of 1 to 8 carbon atoms, benzyl or phenyl, W represents halogen, methoxy or methyl or, in particular, hydrogen, and $R_2$ represents alkyl of 1 to 8 carbon atoms or benzyl.

Preferred sulfone compounds are those of the formula (5) and, in particular, of the formula (3).

Halogen in connection with the substituents in the formulae (1) to (5) is e.g. fluorine, bromine or, preferably, chlorine.

The propenylenesulfone compounds of the formulae (1A) and (1B) are obtained by reacting a vinylene carbenium salt of the formula $$[Y'-CH=CH-CH-Y'']^{\oplus} An^{\ominus} \quad (6)$$

or the carbinol base thereof of the formula $$Y'-CH=CH-\underset{\underset{OH}{|}}{CH}-Y'' \quad (7)$$

with a sulfinic acid of the formula $$Q-SO_2H \quad (8)$$

or a salt thereof, in which formulae (6) to (8) one of $Y'$ and $Y''$ has the meaning of $Y_1$ and the other has the meaning of $Y_2$, and $An^{\ominus}$ is the anion of an inorganic or organic acid and $Y_1$, $Y_2$ and Q are as defined above.

Suitable anions $An^{\ominus}$ are both anions of inorganic acids, e.g. the chloride, bromide, fluoride, sulfate, phosphate or perchlorate ion, and of organic acids, e.g. the acetate ion, or of aromatic or aliphatic sulfonic acids, such as the benzenesulfonate, p-toluenesulfonate, methanesulfonate or ethanesulfonate ion, and also anions of acid alkyl esters of inorganic acids, e.g. the methosulfate or ethosulfate ion.

Salts of the sulfinic acid of the formula (8) are e.g. the alkali metal, alkaline earth metal, ammonium or amine salts.

It is advantageous to carry out the reaction in a polar organic solvent, especially in a lower aliphatic alcohol, for example methanol, ethanol or isopropanol; an ethylene glycol monoalkyl ether, such as ethylene glycol monomethyl or monoethyl ether; or in a cyclic ether, for example tetrahydrofurane or dioxane and preferably in the presence of an acid catalyst. Examples of suitable acid catalysts are lower aliphatic carboxylic acids, such as formic acid or acetic acid, and inorganic acids, such as hydrochloric acid, sulfuric acid, phosphoric acid or perchloric acid.

The reaction can be carried out at a temperature from 10° to 100° C., preferably from 40° to 80° C. The reaction time depends on the temperature and is ordinarily from 5 minutes to 2 hours.

The vinylene carbenium salts of the formula (6) can be obtained according to the method of H. Schmidt and R. Wizinger, Annalen der Chemie, Vol. 623, pp. 204 to 216.

A preferred process for obtaining the carbenium salts of the formula (6) comprises reacting, in acid medium, a compound of the formula $$Y'-CH=CH-E \quad (9)$$

with an aldehyde of the formula $$Y''-CHO \quad (10)$$

wherein E represents hydrogen or carboxyl and $Y'$ and $Y''$ have the given meanings. When E is carboxyl, a decarboxylation is simultaneously effected.

The carbenium salt of the formula (6) is isolated by methods commonly known and employed in the art, e.g. by pouring the reaction mixture into water, whereupon the respective salt precipitates readily, in accordance with the choice of the anion $An^{\ominus}$. The precipitate is collected by filtration, washed and dried. The aqueous solution can also be made alkaline, whereupon the carbinol base of the formula (7) precipitates.

A further mode of obtaining the vinylene carbenium salts of the formula (6) consists in reacting an aldehyde of the formula $$Y'-CHO \quad (11)$$

with the acetyl compound of the formula $$Y''-COCH_3 \quad (12)$$

and reducing the reaction product of the formula $$Y'-CH=CH-CO-Y'' \quad (13)$$

to the carbenium salt of the formula (6), wherein $Y'$ and $Y''$ have the given meanings. The reaction of the aldehyde of the formula (11) with the acetyl compound of the formula (12) can be carried out at a temperature from 10° to 150° C. The reaction medium can be water or a polar organic solvent, preferably a lower aliphatic alcohol. It is advantageous to add an acid condensation agent, e.g. a lower aliphatic carboxylic acid, or a basic condensation agent, preferably a tertiary amine, for example pyridine, triethylamine or triethanolamine, or an alkali metal hydroxide, e.g. sodium hydroxide or potassium hydroxide. The reduction is advantageously carried out in an ether, such as diethyl ether, tetrahydrofurane or dioxane, in the temperature range from 20° to 120° C., preferably at the boiling temperature of the solvent. Suitable reducing agents are e.g. metal hydrides, such as lithium aluminium hydride or sodium borohydride.

The propenylenesulfone compounds of the formulae (1) to (5) are normally colourless or faintly coloured. When these colour formers are brought into contact with an acid developer, e.g. an electron acceptor, then, depending on the meaning of $Y_1$ and $Y_2$, they produce intense red, violet, blue and green shades of excellent lightfastness. They are therefore also very useful when mixed with one or more other known colour formers, for example 3,3-(bis-aminophenyl)-phthalides, 3,3-(bis-indolyl)-phthalides, 3-aminofluoranes, 2,6-diaminofluoranes or spiropyranes, to produce blue, navy blue, grey or black colourations.

The propenylenesulfone compounds of the formulae (1) to (5) exhibit both on clay and on phenolic substrates an improved colour intensity and lightfastness. They are suitable in particular as rapidly developing colour formers for use in a pressure-sensitive recording material, which can also be a copying material.

A pressure-sensitive material consists for example of at least one pair of sheets, which contain at least one colour former of the formulae (1) to (5) dissolved in an organic solvent, and a solid electron acceptor as developer. The colour former effects a coloured marking at those points where it comes into contact with the electron acceptor.

Typical examples of such developers are attapulgite clay, bentonite, acid-activated bentonite, halloysite, montmorillonite, silica, alumina, aluminium sulfate, aluminium phosphate, zinc chloride, kaolin or any clay or acidic organic compound, for example unsubstituted or ring-substituted phenols, salicylic acid or salicylates and their metal salts, or an acidic polymer material, for example a phenolic polymer, an alkylphenolacetylene resin, a maleic acid/colophonium resin or a partially or completely hydrolysed polymer of maleic acid and styrene, ethylene or vinyl methyl ether, or carboxypolymethylene. Mixtures of these polymeric compounds can also be used. Preferred developers are attapulgite clay, acid-activated bentonite, zinc salicylates or the condensation products of p-substituted phenols with formaldehyde. These latter can also contain zinc. These electron acceptors are preferably applied in the form of a layer to the face of the receiver sheet.

In order to prevent the colour formers contained in the pressure-sensitive recording material from becoming active prematurely, they are usually separated from the electron acceptor. This can advantageously be accomplished by incorporating the colour formers in foamlike, sponge-like or honeycomb-like structures. Preferably, the colour formers are enclosed in microcapsules, which as a rule can be ruptured by pressure.

When the capsules are ruptured by pressure, for example with a pencil, and the colour former solution is transferred in this manner to an adjacent sheet which is coated with an electron acceptor, a coloured area is produced. This colour results from the dye which is formed and which is absorbed in the visible range of the electromagnetic spectrum.

The colour formers are encapsulated preferably in the form of solutions in organic solvents. Examples of suitable solvents are preferably non-volatile solvents, for example a polyhalogenated paraffin, such as chloroparaffin, or a polyhalogenated diphenyl, such as trichlorodiphenyl, and also tricresyl phosphate, di-n-butyl phthalate, dioctyl phthalate, trichlorobenzene, trichloroethyl phosphate, an aromatic ether, such as benzylphenyl ether, a hydrocarbon oil, such as paraffin, an alkylated derivative of diphenyl, napthalene or triphenyl, terphenyl, dibenzyl toluene, partially hydrogenated terphenyl, or other chlorinated or hydrogenated, condensed aromatic hydrocarbons.

Mixtures of different solvents are often used in order to obtain an optimum solubility for the colour formation, a rapid and intense colouration, and a viscosity which is advantageous for the microencapsulation.

The capsule walls can be formed evenly around the droplets of the colour former solution by coacervation; and the encapsulating material can consist of gelatin and gum arabic, as described e.g. in U.S. Pat. No. 2,800,457. The capsules can also be formed preferably from an aminoplast or a modified aminoplast by polycondensation, as described in British patent specification Nos. 989,264; 1,156,725; 1,301,052 and 1,355,124. Also suitable are microcapsules which are formed by interfacial polymerisation, e.g. capsules formed from polyester, polycarbonate, polysulfonamide, polysulfonate, but in particular from polyamide or polyurethane.

The microcapsules containing the colour formers of formula (1) can be used for the manufacture of a wide variety of known kinds of pressure-sensitive copying material. The various systems differ substantially from one another in the arrangement of the capsules, the colour reactants and the support.

A preferred arrangement is that in which the encapsulated colour former is in the form of a layer on the back of a transfer sheet and the electron acceptor is in the form of a layer on the face of a receiver sheet. However, the components can also be used in the paper pulp.

Another arrangement of the constituents is that wherein the microcapsules which contain the colour former, and the developer, are in or on the same sheet, in the form of one or more individual sheets, or are present in the paper pulp.

Such pressure-sensitive copying materials are described, for example, in U.S. Pat. Nos. 2,730,457; 2,932,582; 3,418,250; 3,427,180 and 3,516,846. Further systems are described in British patent specification Nos. 1,042,596; 1,042,597; 1,042,598; 1,042,599 and 1,053,935. Microcapsules which contain the colour formers of formula (1) are suitable for each of these systems and for other pressure-sensitive systems.

The capsules are preferably secured to the support by means of a suitable adhesive. Since paper is the preferred support, these adhesives are principally paper-coating agents, for example gum arabic, polyvinyl alcohol, hydroxymethyl cellulose, casein, methyl cellulose or dextrin.

The paper employed comprises not only normal paper made from cellulose fibres, but also paper in which the cellulose fibres are replaced (partially or completely) by synthetic polymer fibres.

The sulfone compounds of the formulae (1) to (5) can also be used as colour formers in a thermoreactive recording material. This recording material contains normally at least one carrier, one colour former, one solid electron acceptor and, if appropriate, also a binder. Thermoreactive recording systems comprise, for example, heat-sensitive recording and copying materials and papers. These systems are used, for example, for recording information, e.g. in electronic computers, teleprinters or telewriters, or in recording and measuring instruments. The image (mark) formation can also be effected manually with a heated pen. Laser beams can also be used to produce heat-induced marks. The thermoreactive recording material can be so composed that the colour former is dispersed or dissolved in one binder layer and the developer is dissolved or dispersed in the binder in a second layer. A second possibility consists in dispersing both the colour former and the developer in one layer. By means of heat the binder is softened at specific areas and the colour former comes into contact with the electron acceptor at those points where heat is applied and the desired colour develops at once.

Suitable developers are the same electron acceptors as are used in pressure-sensitive papers. Examples of developers are the clays and phenolic resins already mentioned, or phenolic compounds, for example 4-tert-butylphenol, 4-phenylphenol, 4-hydroxydiphenyl ether, α-naphthol, β-naphthol, 4-hydroxymethylbenzoate, 4-hydroxyacetophenone, 2,2'-dihydroxydiphenyl, 4,4-isopropylidenediphenol, 4,4'-isopropylidene-bis-(2-methylphenol), 4,4'-bis-(hydroxyphenyl)valeric acid, hydroquinone, pyrogallol, phloroglucinol, p-, m- and o-hydroxybenzoic acid, gallic acid, 1-hydroxy-2-naphthoic acid, as well as boric acid and organic, preferably aliphatic, dicarboxylic acids, for example tartaric acid, oxalic acid, maleic acid, citric acid, citraconic acid and succinic acid.

Fusible, film-forming binders are preferably used for the manufacture of the thermoreactive recording material. These binders are normally water-soluble, whereas the propenylenesulfone compounds and the developers are insoluble in water. The binder should be able to disperse and fix the colour former and the developer at room temperature.

By applying heat the binder softens or melts, so that the colour former comes into contact with the developer and a colour is able to form. Examples of binders which are soluble, or at least swellable, in water are e.g. hydrophilic polymers, for example polyvinyl alcohol, polyacrylic acid, hydroxyethyl cellulose, methyl cellulose, carboxymethyl cellulose, polyacrylamide, polyvinyl pyrrolidone, gelatin and starch.

If the colour former and the developer are in two separate layers, it is possible to use water-insoluble binders, i.e. binders which are soluble in non-polar or only weakly polar solvents, for example natural rubber, synthetic rubber, chlorinated rubber, alkyd resins, polystyrene, styrene/butadiene copolymers, polymethylmethacrylates, ethyl cellulose, nitrocellulose and polyvinyl carbazole. The preferred arrangement, however, is that in which the colour former and the developer are contained in one layer in a water-soluble binder.

The thermoreactive coatings can contain further ingredients. To improve the degree of whiteness, to facilitate the printing of papers, and to prevent the heated pen from sticking, the coatings can contain e.g. talc, $TiO_2$, ZnO, $CaCO_3$, clay or also organic pigments, for example urea/formaldehyde polymers. In order to effect the colour formation only within a limited temperature range, it is possible to add substances such as urea, thiourea, acetamide, acetanilide, stearic amide, phthalic anhydride, phthalic nitrile or other appropriate fusible products which induce the simultaneous melting of the colour former and developer. Thermographic recording materials preferably contain waxes.

In the following Examples, which further illustrate the present invention, the percentages are by weight unless otherwise indicated.

EXAMPLE 1

A mixture of 3.8 g of a vinylene carbenium salt of the formula

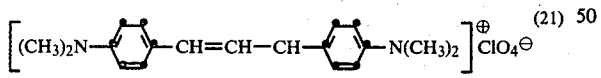
(21)

[obtained by the method of H. Schmidt and R. Wizinger, Annalen der Chemie 623, 204 (1959)], 4 g of sodium p-toluenesulfinate and 1 ml of glacial acetic acid in 50 ml of methanol is refluxed for 10 minutes. The precipitate obtained after cooling is collected by filtration and washed with methanol, affording 3.5 g of a compound of the formula

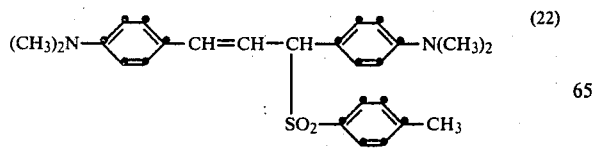
(22)

A sample of this substance recrystallised from toluene melts at 172°–174° C. with decomposition.

When applied to a paper coated with acid-activated bentonite, a solution of the compound of the formula (22) in toluene produces immediately an intense blue, lightfast colour with μ max at 700 nm.

The colour formers of the formula

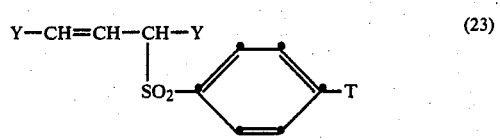
(23)

listed in the following tables are obtained in the same manner as described in Example 1.

TABLE

| Example | Y | T | Shade on acid-activated bentonite |
|---|---|---|---|
| 2 | —⟨⟩—N(C₂H₅)₂ | H | blue |
| 3 | —⟨⟩—N(CH₂—⟨⟩)₂ | H | blue |
| 4 | —⟨⟩—N(—⟨⟩)(C₂H₅) | H | blue |
| 5 | —⟨⟩—N(CH₃)₂ | H | blue |
| 6 | —⟨⟩—N(CH₃)₂ | Cl | blue |
| 7 | —⟨⟩—N⟨pyrrolidine⟩ | CH₃ | blue |
| 8 | —⟨⟩—N(CH₃)—⟨⟩—OCH₃ | H | blue |
| 9 | —⟨⟩(OC₂H₅)—N(C₂H₅)₂ | H | blue |
| 10 | carbazole-N-C₂H₅ | CH₃ | blue |
| 11 | carbazole-N-C₂H₅ (extended) | CH₃ | blue |
| 12 | indoline CH₃, N-C₂H₅ | H | red |

EXAMPLE 13

Production of a Pressure-Sensitive Copying Paper

A solution of 3 g of the propenylenesulfone compound of the formula (22) in 97 g of partially hydrogenated terphenyl is emulsified in a solution of 12 g of pigskin gelatin in 88 g of water of 50° C. A solution of 12 g of gum arabic in 88 g of 50° C. is then added, followed by the addition of 200 ml of water of 50° C. The resulting emulsion is poured into 600 g of ice water, whereupon the coacervation is effected. A sheet of paper is coated with the resulting suspension of microcapsules and dried. A second sheet of paper is coated with acid-activated bentonite. The first sheet and the sheet of paper coated with acid-activated bentonite are laid on top of each other with the coated sides face to face.

Pressure is exerted on the first sheet by writing by hand or typewriter and an intense blue copy of excellent lightfastness develops on the sheet which is coated with clay.

Corresponding intense and lightfast blue and red copies are also obtained by using each of the other colour formers of the formula (23) indicated in Examples 2 to 12 of the table.

EXAMPLE 14

In a ball mill, 32 g of bis-(4-hydroxyphenyl)-dimethylmethane (Bis-phenol A), 3.8 g of the distearylamide of ethylene diamine, 39 g of kaolin, 20 g of an 88% hydrolysed polyvinyl alcohol and 500 ml of water are ground to a particle size of about 5μ. In a second ball mill, 6 g of the compound of the formula (22), 3 g of a 88% hydrolysed polyvinyl alcohol and 60 ml of water are ground to a particle size of about 3μ.

Both dispersions are mixed and applied to paper to a dry coating weight of 5.5 g/m². An intense blue colour of excellent lightfastness is produced by contacting the paper with a heated ball-point pen.

Intense and lightfast blue and red shades can also be obtained by using each of the other colour formers of Examples 2 to 12 of the table.

What is claimed is:

1. A chromogenic propenylenesulfone compound of the formula

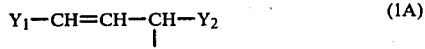

wherein each of $Y_1$ and $Y_2$ independently represents an amino-substituted phenyl radical of the formula

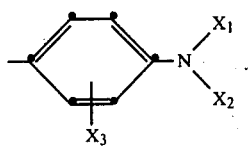

a 3-indolyl radical of the formula

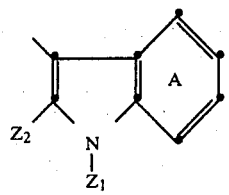

or a 3-carbazolyl radical of the formula

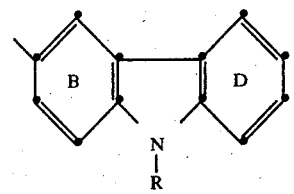

and Q represents alkyl of 1 to 12 carbon atoms or unsubstituted or substituted aryl or aralkyl, whilst each of $X_1$ and $X_2$ independently represents hydrogen, alkyl containing not more than 12 carbon atoms which is unsubstituted or substituted by halogen, hydroxyl, cyano or lower alkoxy, or represents cycloalkyl, phenyl, benzyl, or phenyl or benzyl which is substituted by halogen, lower alkyl or lower alkoxy, or $X_1$ and $X_2$ together with the nitrogen atom to which they are attached represent a pyrrolidino, piperidino, piperolino, morpholino, thiomorpholino or piperazino group, $X_3$ represents hydrogen, halogen, nitro, lower alkyl or lower alkoxy, each of R and $Z_1$ independently represents hydrogen, alkyl containing not more than 12 carbon atoms which is unsubstituted or substituted by halogen, hydroxyl, cyano or lower alkoxy, or represents alkenyl containing not more than 12 carbon atoms, acyl of 1 to 12 carbon atoms, phenyl, benzyl, or phenyl or benzyl which is substituted by halogen, lower alkyl, lower alkoxy or nitro, and $Z_2$ represents hydrogen, lower alkyl or phenyl, the rings A and B, each independently of the other, are unsubstituted or substituted by cyano, nitro, halogen, lower alkyl, lower alkoxy or lower alkoxycarbonyl, and ring D is unsubstituted or substituted by cyano, nitro, halogen, lower alkyl, lower alkoxy, lower alkoxycarbonyl, unsubstituted or substituted phenyl or a fused benzene ring.

2. A compound according to claim 1, wherein $Y_1$ represents a radical of the formula (1a) and $Y_2$ represents a radical of the formula (1a) which is different from $Y_1$, a 3-indolyl radical of the formula (1b) or a 3-carbazolyl radical of the formula (1c).

3. A compound according to claim 1, wherein $Y_1$ and $Y_2$ are identical.

4. A compound according to claim 1, wherein each of $Y_1$ and $Y_2$ represents an amino-substituted phenyl radical of the formula (1a).

5. A compound according to claim 1, wherein each of $Y_1$ and $Y_2$ represents a 3-carbazolyl radical of the formula (1c).

6. A compound according to claim 5, wherein the ring D in formula (1c) contains one or two fused benzene rings.

7. A compound according to claim 1, wherein Q represents an unsubstituted or substituted aryl radical.

8. A compound according to claim 1 of the formula

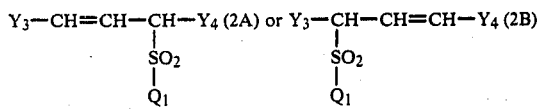

wherein each of $Y_3$ and $Y_4$ independently represents an amino-substituted phenyl radical of the formula

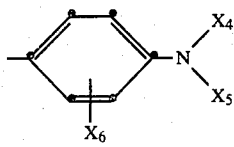

a 3-indolyl radical of the formula

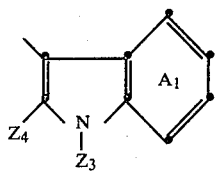

or a 3-carbazolyl radical of the formula

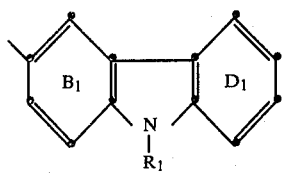

and $Q_1$ represents alkyl of 1 to 12 carbon atoms, or an unsubstituted or substituted aryl radical, whilst each of $X_4$ and $X_5$ independently represents lower alkyl, phenyl, lower alkylphenyl, lower alkoxyphenyl or benzyl, and $X_4$ also represents hydrogen, or $X_4$ and $X_5$ together with the nitrogen atom to which they are attached represent pyrrolidino, piperidino or morpholino, $X_6$ represents hydrogen, halogen, lower alkyl or lower alkoxy, each of $R_1$ and $Z_3$ independently represents alkyl of not more than 12 carbon atoms which is unsubstituted or substituted by halogen, cyano or lower alkoxy, or represents lower alkylcarbonyl, phenyl, or benzyl which is unsubstituted or substituted by halogen, lower alkyl or lower alkoxy, and $Z_3$ also represents hydrogen and $Z_4$ represents hydrogen, methyl or phenyl, the rings $A_1$ and $B_1$, each independently of the other, are unsubstituted or substituted by cyano, halogen, lower alkyl or lower alkoxy and ring $D_1$ is unsubstituted or substituted by cyano, halogen, lower alkyl, lower alkoxy or one or two fused benzene nuclei.

9. A compound according to claim 8, wherein each of $Y_3$ and $Y_4$ in formula (2) represents an amino-substituted phenyl radical of the formula (2a) or a carbazolyl radical of the formula (2c).

10. A compound according to claim 8, wherein $Q_1$ in formula (2) represents phenyl or phenyl which is substituted by halogen, methyl or methoxy.

11. A compound according to claim 8 of the formula

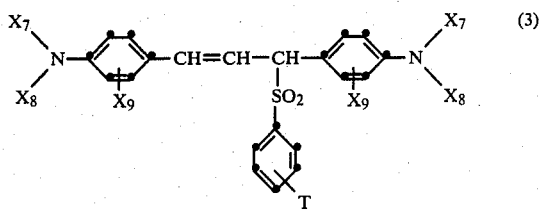

wherein $X_7$ represents lower alkyl, phenyl, lower alkylphenyl, lower alkoxyphenyl or benzyl, $X_8$ represents hydrogen, lower alkyl or benzyl, $X_9$ represents hydrogen, methyl, methoxy or ethoxy, and T represents hydrogen, halogen, methyl or methoxy.

12. A compound according to claim 8 of the formula

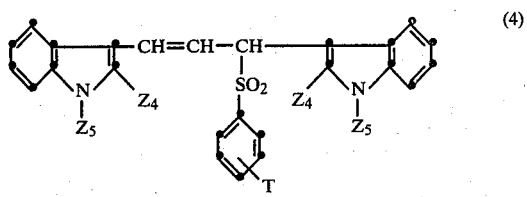

wherein $Z_4$ represents hydrogen, methyl or phenyl, $Z_5$ represents hydrogen, acetyl, alkyl of 1 to 8 carbon atoms, benzyl or phenyl, and T represents hydrogen, halogen, methyl or methoxy.

13. A compound according to claim 8 of the formula

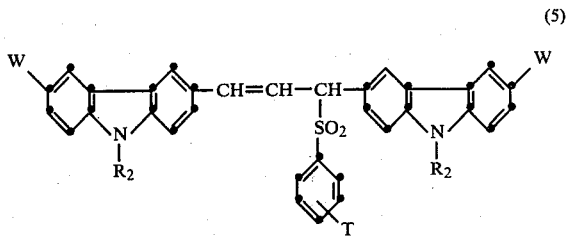

wherein $R_2$ represents alkyl of 1 to 8 carbon atoms or benzyl, W represents hydrogen, halogen, methoxy or methyl, and T represents hydrogen, halogen, methyl or methoxy.

14. A compound according to claim 13, wherein W in formula (5) represents hydrogen.

15. A compound according to claim 6, wherein the ring D in formula (1c) together with the fused benzene nuclei completes a 1,2-benzocarbazolyl, 3,4-benzocarbazolyl or 1,2,3,4-dibenzocarbazolyl radical.

16. A compound according to claim 7, wherein Q represents phenyl, diphenyl, naphthyl or phenyl substituted by halogen, cyano, nitro, lower alkyl, lower alkoxy, methylene-dioxy, or acyl of 1 to 8 carbon atoms.

* * * * *